United States Patent [19]
Castor et al.

[11] Patent Number: 5,743,253
[45] Date of Patent: Apr. 28, 1998

[54] METHOD AND APPARATUS FOR MAINTAINING A DEFINED RESPIRATORY GAS FLOW PATTERN TO A SUBJECT BY IDENTIFYING A TRANSFER FUNCTION OF THE CONNECTION SYSTEM

[75] Inventors: Rolf Castor, Hägersten; Göran Cewers, Lund; Rolf Wernbro, Malmö; Magnus Nord, Bromma, all of Sweden

[73] Assignee: Siemens-Eleman AB, Solna, Sweden

[21] Appl. No.: 588,684

[22] Filed: Jan. 19, 1996

[30] Foreign Application Priority Data

Jan. 26, 1995 [SE] Sweden .................................. 9500275

[51] Int. Cl.⁶ .................................................. A61M 15/00
[52] U.S. Cl. ............................. 128/200.24; 128/204.21; 128/204.23
[58] Field of Search ................... 128/200.24, 204.18, 128/204.21, 204.23, 203.12

[56] References Cited

U.S. PATENT DOCUMENTS

| | | | |
|---|---|---|---|
| 4,393,869 | 7/1983 | Boyarsky et al. | 128/204.18 |
| 4,991,576 | 2/1991 | Henkin et al. | 128/203.12 |
| 5,303,698 | 4/1994 | Tobia et al. | 128/204.21 |
| 5,365,922 | 11/1994 | Raemer | 128/204.21 |
| 5,577,496 | 11/1996 | Blackwood et al. | 128/204.21 |

OTHER PUBLICATIONS

Siemens Elema Servo Ventilator 300 Operating Manual, pp. 94–98 (1993).
Puritan–Bennet 7200 Series Microprocessor Ventilator, Option 30/40 (Mar. 1986).
"Modellbygge-Och Simulering," Ljung et al. pp. 232–239 (1991).
System Identification: Theory for the User, Ljung, pp. 69–81.

Primary Examiner—Aaron J. Lewis
Attorney, Agent, or Firm—Hill, Steadman & Simpson

[57] ABSTRACT

A ventilator system has different sub-systems, such as a connection system, which influence the flow of breathing gas supplied to a patient's respiratory system. The flow pattern of the breathing gas is particularly influenced by the connection system. In order to compensate for this influence to the greatest possible extent in the generation of breathing gas, the connection system's transfer function is determined before the system is connected to the respiratory system. A gas flow with a specific gas flow pattern is generated with high accuracy in a ventilator unit. An ensuing gas flow pattern, only influenced by the connection system, is measured with high accuracy in a measurement unit in the ventilator unit. The transfer function for the connection system can be determined in a control unit from the known, generated gas flow pattern and the measured, ensuing gas flow pattern. The corresponding determination can be made for the respiratory system after a patient has been connected.

20 Claims, 3 Drawing Sheets

METHOD AND APPARATUS FOR MAINTAINING A DEFINED RESPIRATORY GAS FLOW PATTERN TO A SUBJECT BY IDENTIFYING A TRANSFER FUNCTION OF THE CONNECTION SYSTEM

BACKGROUND OF THE INVENTION

1. Field of the Invention

The present invention relates to a method and apparatus for determining a transfer function, at least with respect to the parameters of pressure and flow, for a connection system in a ventilator system, the connecting system connecting the respiratory system of a living subject to a ventilator unit of the ventilator system for supplying and carrying off a breathing gas to/from the respiratory system with a predetermined gas flow pattern. The transfer function designates the way in which the connection system influences the predetermined gas flow pattern and can be used to compensate regulation of the pressure and flow of the breathing gas.

2. Description of the Prior Art

In the past 50 years, the development of ventilator systems (respirator systems) has made rapid progress. From initially using simple mechanical piston systems to impose breathing gas on the patient at every piston stroke, today's ventilator systems can be controlled to supply a breathing gas to a patient according to a number of different operating modes, a physician then being able to select the operating mode deemed most suitable for the patient.

One such ventilator is the Servo Ventilator 300, manufactured and sold by SiemensElema AB, Solna, Sweden. This ventilator is equipped with a very fast and accurate gas regulation system. In practice, this means that a gas flow can be generated with an optional gas flow pattern. In the present application, "gas flow pattern" refers to pressure and flow characteristics over time. Pressure and flow in any given gas flow pattern can exhibit predefined variations over time. Even if the regulatory system is capable of delivering a gas flow which corresponds almost exactly to a target gas flow pattern, however, it is not certain that the gas flow received by the patient has the target gas flow pattern. This is because the connection system, disposed between the ventilator unit of the overall system and the respiratory system of the patient, influences the gas flow pattern. The connection system can, e.g., comprise tubes, humidifiers, dehumidifiers, bacterial filters, etc. Flow resistance in gas lines and other components in the connection system influences gas flow in one way. The total volume occupied by the connection system influences gas flow in another way. This is because gases are highly compressible. The influence to which gas flow is subjected in the connection system changes the pattern of gas flow with respect to delay and morphology (morphology here referring to variations in pressure and flow over time).

Attempts have been made to compensate, at least to some extent, for this influence by the connection system. For example, an Operating Manual for the aforementioned Servo Ventilator 300, AG 0593 3.5, Siemens-Elema AB, 1993, pp. 94–98, describes compensation for the connection system's compressible volume. Such compensation entails the physician setting a larger minute volume for the breathing gas to be supplied to the patient to ensure delivery to the patient of the target minute volume. The physician is required to make the calculations to achieve the necessary compensation. The calculation example on page 98 in the manual for an adult patient shows that minute volume had to be increased by 2.5 liters per minute when the target minute volume was 7.5 liters per minute. Compensation naturally varies from case to case. The need for compensation depends in particular on the connection system's configuration. However, the calculation example does provide an indication of the compensation needed for minute volume.

There are also other known ventilator systems offering compensation, either by a physician or by a programmed automatic function. The compensation mainly entails a determination of the connection system's compressible volume, e.g., the Puritan-Bennett, 7200 series Microprocessor Ventilator, Option 30/40, Part Number 20522A, March 1986.

Determination of compressible volume, however, does not really indicate how a gas flow's gas flow pattern is actually influenced in the connection system. As noted above, "gas flow pattern" refers to pressure and flow variation over time. If the flowing gas is viewed as a gas column passing through the connection system, it will be realized that even simple compression of the gas column changes the column's characteristics and, in particular, its pressure and flow variations. Thus, compressible volume does not indicate anything about, e.g., the way in which a target pressure increase for the gas column is influenced on its way to the patient's respiratory system. Determining compensation for the connection system's compressible volume therefore does not supply sufficient information for use in calculating compensation of the gas flow pattern. As already noted, the flow of gas is also delayed in the connection system.

In conjunction with both the diagnosis and treatment of disorders in the respiratory system (primarily the lungs) of a patient, determination of the various mechanical parameters of the lungs is desirable. Determination of resistance and compliance is especially important. Roughly speaking, compliance can be determined in ways similar to determinations of compressible volume in the connection system of the known ventilator systems. A problem, however, is that the connection system's influence on gas flow is not fully known, so determination of the mechanical parameters of the lungs is uncertain. Moreover, the properties of these mechanical parameters can also influence the gas flow's flow pattern.

In conjunction with the development of increasingly accurate and exact systems in the ventilator art, the ability to determine and take into account factors for which compensation previously could not be made is also desirable.

SUMMARY OF THE INVENTION

An object of the invention is to provide a method for more accurate determination of a transfer function for a connection system between a ventilator unit and a respiratory system.

Another object of the invention is to provide a method for determining, with greater accuracy than heretofore, the influence of the respiratory system on the flow pattern of a gas.

An additional object is to provide a method for determining, with greater accuracy than heretofore, the respiratory system's various parameters, such as resistance and compliance.

Yet another object of the invention is to provide an apparatus which can be connected to a respiratory system in order to supply and remove breathing gas according to a specific gas flow pattern and which can compensate for the interposed connection system's influence on the gas flow pattern.

A method for determining the transfer function in accordance with the invention includes the following steps:

connection of the connection system to the ventilator unit; supply of a gas with a first test gas flow pattern from a gas-regulating unit in the ventilator unit, measurement in a measurement unit of an ensuing response gas flow pattern for the gas; and determination of the transfer function from the test gas flow pattern and the response gas flow pattern. Once the transfer is determined, it is used to compensate settings at the ventilator unit for producing a defined (therapeutic) gas flow pattern at the respiratory system. These settings may (and likely will) deviate slightly from settings which would produce the defined pattern in the absence of the connection system. The transfer function determination enables the influence of the connection system on the gas flow to be taken into account to be sure that the defined pattern is, in fact, present at the respiratory system.

In principle, this procedure resembles determination of the transfer function for unknown systems in electronics (e.g. automatic control), however, there are major differences. Firstly, gases have very specific properties which are hard to establish, as regards flow and compressibility. Secondly, regulation of a gas flow with sufficient accuracy to permit reliable determination of what the gas flow pattern should look like has hitherto been impossible in the ventilator art. Especially in respect to varying pressure and flow over time, earlier systems have not been able to achieve this with the rapidity and accuracy sufficient to ensure that the emitted gas flow really possesses the desired gas flow pattern.

Mathematical determination of the transfer function can be performed in a number of known ways. One possibility is to use the flow and pressure of the gas fed to the connection system as input signals for the connection system and to use the flow and pressure of gas having passed through the entire connection system as output signals for the connection system. Alternatively, all these flows and pressures can be used as input signals for the connection system, and flow and pressure are measured at the part of the connection system, which is to be connected to the respiratory system, and used as output signals. A mathematical model structure, e.g. a Box-Jenkins model structure, is then used and adapted to the measurement values. Generally speaking, the Box-Jenkins model can be described (in discrete form) as follows:

$$y(t)=G(q,\theta)u(t)+H(q,\theta)e(t),$$

in which u(t) is the input signal for the connection system and y(t) is the output signal. The Box-Jenkins model is well known and described in the automatic control literature, e.g. in "Modellbygge och simulering" by L. Ljung and T. Glad (p. 234), Studentlitteratur Lund, 1991. The above model is described in the one-dimensional case in the this book, whereas it has been generalized into multiple dimensions for application to the model according to the invention, i.e. the above model is a matrix equation.

In determination of the transfer function, it is advantageous to employ a lung model with known characteristics with the connection system for determination of the transfer function. The lung model suitably contains a flow meter and pressure meter for generating the connection system's output signals.

A refinement of the method is achieved in a further embodiment of the invention, including the following additional steps: connection of the connection system to the respiratory system; supply of a gas with a second test gas flow pattern from the gas-regulating unit in the ventilator unit; measurement in the measurement unit of an ensuing second response gas flow pattern for the gas; and determination of the respiratory system's influence on the flow pattern of the gas flow from the second test gas flow pattern, the second response gas flow pattern and the determined transfer function.

If the connection system and the respiratory system are regarded as two interconnected systems, the characteristics of the respiratory system and its influence on a gas flow's flow pattern can be determined when the way the connection system influences the gas flow pattern is taken into account. This influence is known from determination of the transfer function, so the influence of the respiratory system can be determined more accurately than has heretofore been possible. In principle, the same test gas flow pattern can be used for determining both the transfer function and the influence of the respiratory system.

It is advantageous for the test gas flow pattern to have a frequency spectrum corresponding to the different frequency spectra present in the ventilation modes in which the ventilator unit is capable of operating.

In order to obtain an optimum transfer function for all types of connection systems, the transfer function can be determined from a number of preprogrammed model structures, preferably both linear and non-linear, all model structures being adapted to the measurement values and the model structure having the highest correlation is selected as the transfer function.

An apparatus for performing the method in accordance with the invention has a ventilator unit and a connection system, connected to the ventilator unit and connectable to the respiratory system, the ventilator unit including a gas-regulating unit, with at least one flow meter and a pressure meter in an inspiratory section of the ventilator unit, in order to generate a breathing gas flow with a specific gas flow pattern, and a measurement unit with a flow meter and a pressure meter in an expiratory section of the ventilator unit, for measuring the gas parameters pressure and flow, and a compensation unit, connected to the measurement unit and the gas-regulating unit, for determining the connection system's transfer function for the breathing specific flow pattern of the gas flow.

In an embodiment of the apparatus the compensation unit is devised to determine the transfer function from the use of measurement signals from the meters in the inspiratory section as the connection system's input signals and measurement signals from the meters in the expiratory section as output signals. This corresponds to the first case described above.

In this context, the apparatus can further include a diagnostic unit connected to the measurement unit and the compensation unit in order to determine at least one mechanical lung parameter related to the subject's respiratory system. The diagnostic unit may determine one or both of the mechanical lung parameters of resistance and compliance.

In another embodiment of the apparatus in accordance with the invention, the measurement unit further includes a test lung, connectable to the connection system, a flow meter and/or pressure meter being arranged in the test lung to measure flow and/or pressure, and the compensation unit determines the transfer function from the use of measurement signals from the meters in the inspiratory section and expiratory section as the connection system's input signals and measurement signals from the meters in the test lung as output signals. This corresponds to the second case described above. It should be noted that sufficient information can be obtained by only studying the transfer function with respect to flow or pressure. The test lung can advantageously be integrated into the ventilator unit.

The compensation unit can be devised to calculate a compensation factor, which can be sent to the gas-regulating unit, changing its emission of breathing gas with the determined gas flow pattern so the breathing system receives a breathing gas flow essentially in accordance with the determined gas flow pattern. Once the transfer function is known, control of gas supply can easily be compensated so the patient really receives the intended gas flow pattern.

DESCRIPTION OF THE PREFERRED EMBODIMENTS

Figure 1:
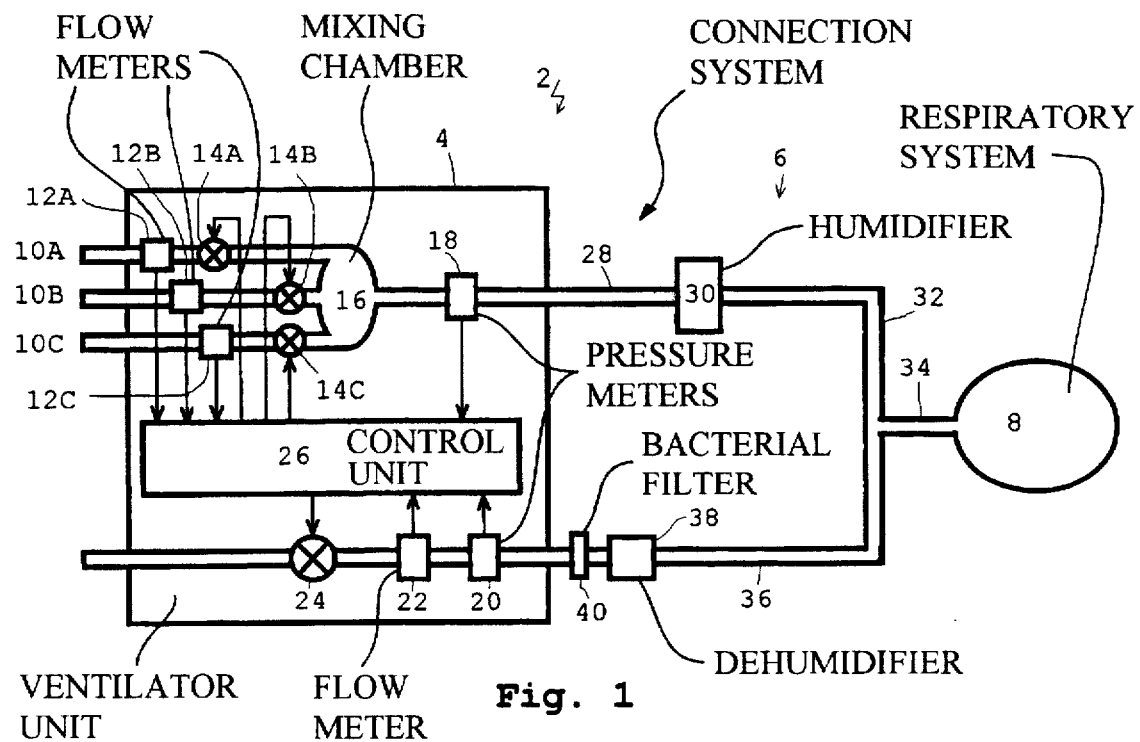
FIG. 1 is a block diagram of a ventilator system constructed and operating in accordance with the principles of the present invention.

The ventilator system 2 shown in FIG. 1 has a ventilator unit 4 and a connection system 6 and is connected to the respiratory system 8 of a living subject. The respiratory system 8 is supplied with a breathing gas, via the connection system 6, from the ventilator unit 4. Gas expired from the respiratory system 8 is returned to the ventilator unit 4 via the connection system 6. In principle, the ventilator unit 4 can be a modified Servo Ventilator 300, Siemens-Elema AB, Solna, Sweden.

The ventilator unit 4 has an inspiratory section and an expiratory section. Three gas connections 10A, 10B and 10C are arranged at the inspiratory section. Up to three gas sources can be connected to them for supplying gases to the ventilator unit 4. For example, existing, high-pressure piped air and oxygen supplies in hospitals can be connected to the gas connections 10A, 10B and 10C. Alternatively, mobile pressurized gas cylinders or bottles can be used.

A first flow meter 12A, a second flow meter 12B and a third flow meter 12C are arranged in the inspiratory section of the ventilator unit 4 at each gas connection 10A, 10B and 10C to measure the flow of a gas passing therethrough. A first inspiratory valve 14A, a second inspiratory valve 14B and a third inspiratory valve 14C are also arranged by each gas connection 10A, 10B and 10C to regulate a flow of gas. The supplied gases are mixed in a mixing chamber 16 into the breathing gas which is to be supplied to the respiratory system 8. A first pressure meter 18 is also arranged in the inspiratory section of the ventilator unit 4 to measure the pressure of the breathing gas.

Gas expired from the respiratory system 8 is conveyed to the expiratory section of the ventilator unit 4. A second pressure meter 20 and a fourth flow meter 22 are arranged in this section to measure the gas parameters pressure and flow. An expiratory valve 24, also arranged in the expiratory section of the ventilator unit 4, is mainly for regulating any counter-pressure during expiration, i.e. PEEP (post-expiratory end pressure). All functions of the ventilator unit 4 are controlled and regulated by a control unit 26. The inspiratory valves 14A, 14B, 14C, the flow meters 12A, 12B, 12C and the control unit 26 are included with the control unit 26 as elements of a gas-controlling means.

The connection system 6 can include a number of different components, depending in part on the type of treatment to be performed and in part on the patient to be connected to the ventilator system 2. The connection system 6 normally has an inspiratory line 28, which carries breathing gas to the patient, a humidifier 30 to keep the patient's lungs from drying out, a Y-connector 32, a tracheal tube 34, an expiratory line 36, which carries expired gas back to the ventilator unit 4, a dehumidifier 38 to prevent the formation of condensation in the flow meter 22, and a bacterial filter 40 to prevent contamination of the ventilator unit 4.

The connection system 6 influences the flow pattern of the breathing gas generated and supplied by the ventilator unit 4. This influence will depend on, e.g., the components forming the connection system 6 and the properties of these components. For example, the length of each of the inspiratory tube 28 and the expiratory tube 36 influences the gas flow pattern. Even the elasticity of the inspiratory tube 28 and the expiratory tube 36 influence the gas flow pattern. The other components mentioned above also influence the gas flow pattern in unknown ways. This means that a target gas flow pattern, generated by the ventilator unit 4, is changed in the course of its passage through the connection system 6. The gas flow pattern received by the respiratory system 8 will then deviate from the target gas flow pattern.

Generation of the breathing gas flow in the ventilator unit 4 must therefore be compensated for the influence of the connection system 6 for reliable supply of a breathing gas flow, with a predefined gas flow pattern, to the respiratory system 8. The requisite compensation is automatically determined by the ventilator unit 4 for every unique setup of the connection system 6. In practice, this is performed when the ventilator system 2 is first set up and prepared for connection to a patient. Before the patient is connected, a test routine is performed in order to determine the transfer function for the connection system 6 setup. Here, the transfer function designates the influence of the utilized connection system 6 on the flow pattern of an inflowing gas flow pattern. Generation of the breathing gas with a specific gas flow pattern can then be compensated for this influence, and the patient can receive a breathing gas flow which complies as accurately as possible with the breathing gas flow pattern selected by the physician for the patient.

Figure 2:
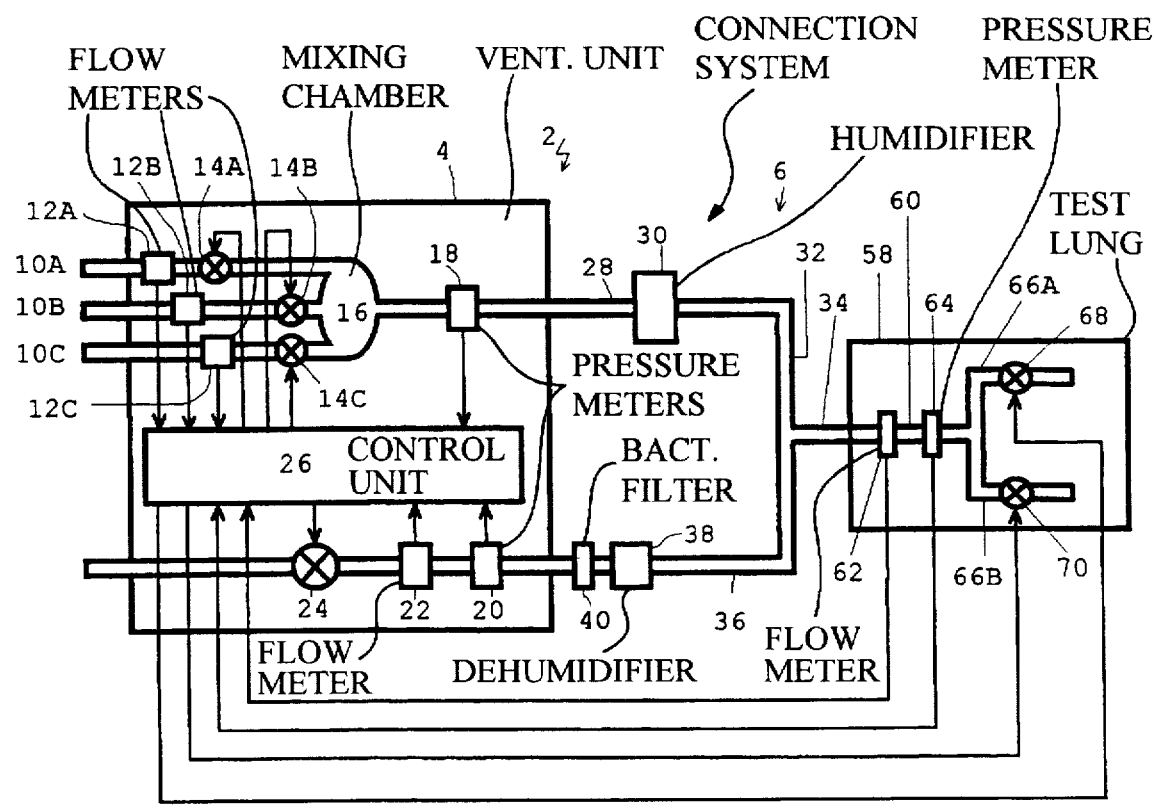
FIG. 2 is a block diagram of the ventilator system of FIG. 1 connected to a test lung.

FIG. 2 shows a version for testing the connection system 8. In this instance, a test lung 58 has been connected to the connection system 6. The test lung 58 contains a tube 60, connected to the Y-connector 32 or the tracheal tube 34, a fifth flow meter 82 and a third pressure meter 64, both connected to the control unit 26, for sending measurement values to the control unit 26. In addition, the tube 60 is subdivided into a first line 66A in which a first test lung valve 68 is arranged, and a second line 66B in which a second test lung valve 70 is arranged. The passage of all types of breathing gas through the test lung 58 can be simulated. In addition, factual measurement values for the gas flow pattern which actually reaches the simulated breathing system are also obtained.

It should be noted that the use of a flow meter and a pressure meter by the tracheal tube 34 in FIG. 1, when a breathing system 8 is connected, makes it possible for measurement results from the test lung 58 to be used in rapidly establishing the type of breathing system. If, e.g., a number of combinations of resistance and compliance have been simulated in the test lung 58, relatively reliable information on the breathing system's resistance and compliance can be obtained directly.

Figure 3:
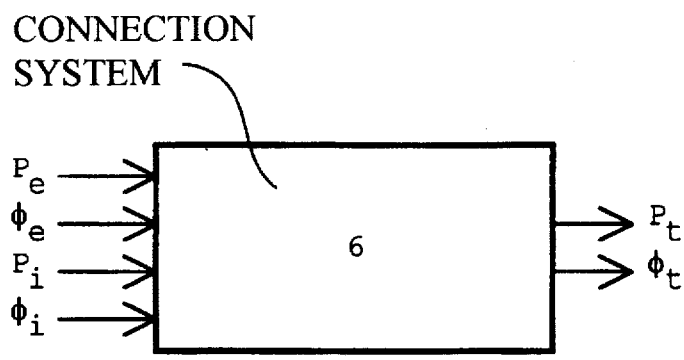
FIGS. 3 and 4 schematically illustrate respective models for determining the transfer function of the connection system in the ventilator systems of FIGS. 1 and 2 in accordance with the principles of the present invention.

FIG. 3 shows a first model for determining the transfer function for the connection system 6. The calculation model can be used for the setup according to FIG. 2. Gas pressure $P_i$ (inspiratory pressure), measured in the first pressure meter 18, total gas flow $\Phi_i$ (inspiratory flow), measured in the first, second and third flow meters 12A, 12B and 12C, gas pressure $P_e$ (expiratory pressure), measured in the second pressure meter 20, and gas flow $\Phi_e$ (expiratory flow), measured in the fourth flow meter 22, are used as input signals. Output signals from this system are measurement values from the test lung 58, i.e., the pressure $P_t$ measured in the third pressure meter 64, and flow $\Phi_t$. All the signals $P_i$, $\Phi_i$, $P_e$, $\Phi_e$, $P_t$ and $\Phi_t$ vary with time, and the transfer function for the connection system 6 designates the output signal which a predefined input signal produces. By assigning a model structure for the transfer function and adapting it to the measured input and output signals under given conditions, predefined output signals can be obtained with high accuracy by calculation, via the transfer function, of the input signals needed to generate the predefined output signals.

Determination of the transfer function can be performed by applying a known automatic control technic. For example, a Box-Jenkins model structure can be employed as the transfer function. This model has the general structure:

$$Y(t)=G(q,\theta)u(t)+H(q,\theta)e(t)$$

in which Y(t) is the column vector $[P_t(t), \Phi_t(t)]$, i.e. the output signals. $G(q,\theta)$ is a matrix with a time displacement operator q and a weighting function $\theta$) which operates on the input signals u(t), i.e. the column vector $[P_i(t), P_e(t), \Phi_i(t), \Phi_e(t)]$. H (q, $\theta$) corresponds to G(q, $\theta$) and operates on e(t) which consists of white noise. This and similar model structures are well-known and described in the technical literature, especially in literature on automatic control. A detailed description of the purely mathematical calculations for determining the weighting function is therefore not necessary.

A second model for determining the transfer function for the connection system 6. The calculation model can be used for the setup according to FIG. 1 before the respiratory system 8 is connected to the connection system 6. Measurements can be made without a test lung or with one or more test lungs with predetermined properties. In this model, inspiratory pressure $P_i$ and inspiratory flow $\Phi_i$ are used as input signals, and expiratory pressure $P_e$ and expiratory flow $\Phi_e$ are used as output signals. A model structure similar to the one used above can be advantageously used even in this model.

Figure 4:
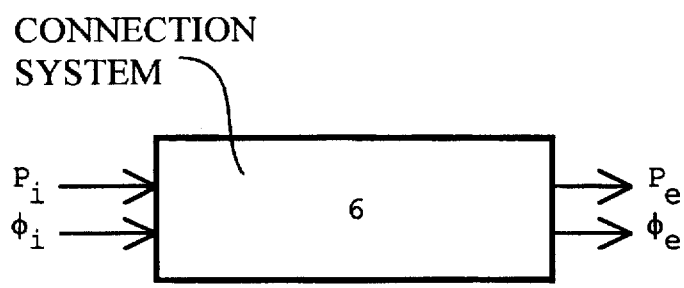

The main differences between the two models in FIG. 3 and FIG. 4 can be described as follows. With the model according to FIG. 3, a transfer function is obtained which describes, as accurately as possible, the way the gas flow pattern will behave at the tracheal tube 34, i.e. when connected to the respiratory system. When this behavior is known, a patient can be supplied with a well-defined, predetermined gas flow pattern. The influence of the respiratory system 8 on the entire system, however, cannot be calculated (unless the pressure and flow meters are used in direct conjunction with the respiratory system 8, as with the test lung 58). The influence of the respiratory system 8 can only be determined indirectly, as noted above. The model according to FIG. 4 can advantageously be used for determining the way the respiratory system 8 influences the entire system, and the properties of the respiratory system 8 can accordingly be determined more accurately than has heretofore been possible. This can only be accomplished with a tradeoff, viz. the gas flow pattern to the respiratory system 8 cannot be regulated with the same accuracy as in the first model.

Simultaneous determination of a transfer function according to both models, however, is no problem, since all the signals are accessible when the first model is applied.

Figure 5:
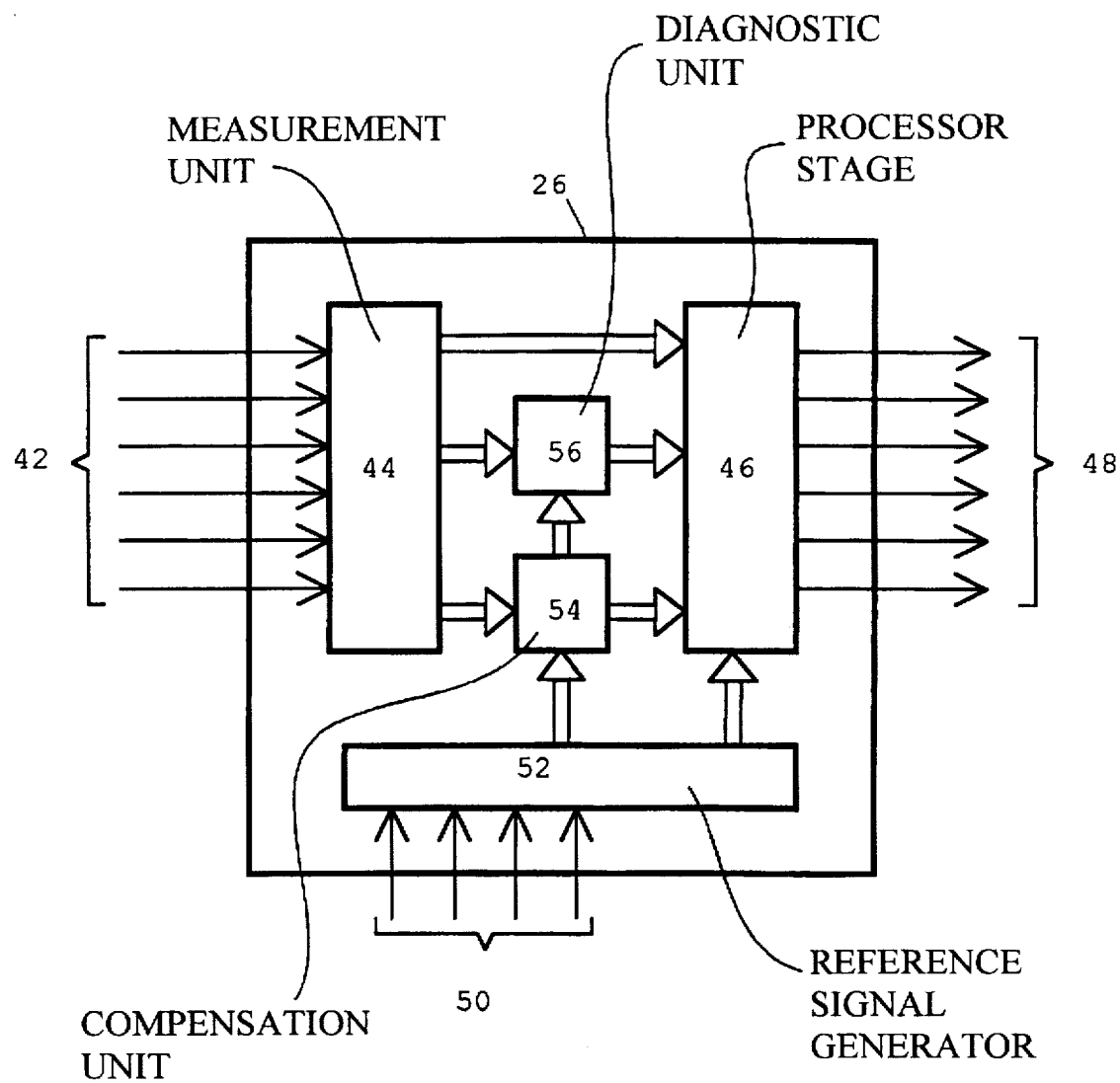
FIG. 5 is a schematic block diagram of a control unit in the ventilator systems of FIGS. 1 and 2.

FIG. 5 is a block diagram of the components in the control unit 26 needed to perform control of the ventilator unit 4. The measured values for flow and pressure are sent to a measurement unit 44 in the control unit 26 via a number of measurement signal input terminals 42.

Some signal processing, such as filtering, amplification, differentiation and/or integration can be performed in the measurement signal unit 44. Integration of the flow signal provides a value for supplied, or outflow, gas volume to/from the connection system 6. The processed measurement signals are also digitized and then sent from the measurement unit 44 to a processor stage 46.

The signals are used in the processor stage 46 for effecting control of the ventilator unit 4, and control signals are emitted via a number of control signal output terminals 48. The control signals can consist of control signals for the inspiratory valves 14A, 14B, 14C and the expiratory valve 24. The control signals can also be used for controlling alarm functions and display units which are not shown but which are normally part of the ventilator unit 4. The Servo Ventilator 300 is a typical example of a modern ventilator containing a number of components and functions which need not be specified in more detail in this context.

In the determination of control signals for e.g. the valves 14A, 14B, 14C, 24 in the ventilator unit 4, the control unit 46 receives reference signals via a reference signal generator 52. The reference signal generator 52 is, in turn, connected to a reference input terminal 50 via some form of interface with a physician, i.e. a control panel used by the physician to program a target operating mode for the ventilator unit 4. This target operating mode is registered by the reference signal generator 52 which generates the requisite reference signals for controlling the ventilator unit 4.

A compensation unit 54 is connected to the reference signal generator 52 and to the measurement signal unit 44. When an initial calculation of the transfer function for the connection system 6 is to be made, the compensation unit 54 is supplied with information about how the test gas to be generated is devised, i.e. which test gas flow pattern the test gas is to have, via the reference signal generator 52. This could involve, e.g., sharp step functions or some form of so-called chromatic noise. The test gas flow pattern could advantageously even contain all the gas flow patterns occurring in the operating modes which could be used with the breathing system.

The compensation unit 54 then receives a response gas flow pattern from the measurement unit 44, i.e. the gas flow pattern ensuing after the influence of the connection system 6. As previously noted, this can consist of one or a number of the above-described models. With known input signals and known output signals for the connection system 6, the compensation unit 54 can then calculate the transfer function for the connection system 6, and this result is sent to the processor stage 46 which can then formulate the control signals at the output terminals 48 so as to compensate control of the ventilator unit 4 so the true gas flow pattern with which breathing gas is supplied to the patient is as similar as possible to the gas flow pattern selected by the physician.

A diagnostic unit 56 is also arranged in the control unit 26. The diagnostic unit 56 is connected to the measurement unit 44 and to the compensation unit 54. After the patient has been connected to the device ventilator system 2, a number of different mechanical lung parameters can be accurately determined for the patient's lungs, e.g. resistance and compliance. This is accomplished as described above, i.e. when the diagnostic unit 56 receives factual measurement values from the measurement unit 44, reference values for the target flow pattern for the breathing gas, and the determined transfer function from the compensation unit 54. The target lung parameters are determined thereafter. On the basis of this information, the diagnostic unit 56 can also determine the patient's transfer function in the ventilator system 2.

More accurate values and more exact models, which are more sensitive to the different properties of the gases, can be used as the result of more accurate determination of the transfer function than has heretofore been possible. With a better mathematic model, the viscosity of the breathing gas, for example, can also be taken into account.

The block diagram in FIG. 5 only shows a schematic, functional structure for the control unit 26, but it can be realized in different ways. The determinations can be made with hardware or software. Analog and digital elements can be combined when suitable. The control unit 26 also contains means for performing a number of unspecified, known functions necessary to the operation of the ventilator system 2.

Another possible, direct application of the present invention concerns control of the expiratory valve 24 to maintain a predefined value for PEEP. When an exhalation (expiration) is to commence, the expiratory valve 24 opens completely to release gas from the respiratory system 8. In principle, this flow constitutes a step function. Flow will then decline in a way resembling a capacitor's discharge curve. Before flow ceases completely, the expiratory valve 24 is activated toward the closed position so as to maintain the predefined value for PEEP. A simplified transfer function for this specific phase of a breathing cycle is obtained by measuring the flow's time constant. The time constant can be used for improving regulation of the expiratory valve 24 so it can stay open longer while simultaneously maintaining the PEEP level with greater accuracy.

A number of versions of the described embodiments can clearly be envisioned. For example, transfer function models could be applied solely to pressure or flow. The test lung 58 could be devised in a number of ways, with or without meters, or it could be built into the ventilator unit 4. Known model structures other than the Box-Jenkins model can be used. A number of model structures can be applied simultaneously, and the one exhibiting the highest correlation between input signals and output signals for a given connection system then being used. The ventilator system 2 can be devised so the transfer function is automatically determined every time the ventilator unit 4 is activated, but it can also be devised so that a transfer function determination must be ordered by staff. The model structure for the transfer function can be a non-linear function of a higher order, as well as linear. Different transfer functions can be determined for special operating modes, or sub-stages, in the operation of the ventilator system 2.

Although various changes and modifications to the presently preferred embodiments described herein will be apparent to those skilled in the art, such changes and modifications can be made without departing from the spirit and scope of the present invention and without diminishing its intended advantages. Therefore, the appended claims are intended to cover such changes and modifications.

We claim as our invention:

1. A method for regulating the supply of breathing gas to and the removal of expired gas from the respiratory system of a subject in a ventilator system having a ventilator unit connectable to the respiratory system of the subject, said method comprising the steps of:

connecting a connection system to said ventilator unit, said connection system having a transfer function associated therewith identifying an influence of said connecting system on gas pressure and gas flow in said connection system;

setting a test gas flow pattern in said ventilator unit and supplying gas with said test flow pattern to said connection system;

measuring a response gas flow pattern arising from said test gas flow pattern;

determining said transfer function from said test gas flow pattern and said response gas flow pattern;

selecting a therapeutic gas flow pattern; and setting a compensated gas flow pattern at said ventilator unit, dependent on said transfer function, for producing said selected therapeutic gas flow pattern, via said connection system, at said respiratory system of said subject.

2. A method as claimed in claim 1 comprising the additional step of connecting a lung model having known characteristics to said connection system during supply of said test gas flow pattern.

3. A method as claimed in claim 2 wherein the test gas flow pattern supplied to said connection system with said lung model connected to said connection system comprises a first test gas flow pattern, and said method comprising the additional steps of:

removing said lung model and connecting said connection system to the respiratory system of the subject;

supplying a second test gas flow pattern from said ventilator unit to the respiratory system via said connection system;

measuring a second response gas flow pattern arising from said second test gas flow pattern;

determining an influence of said respiratory system on gas flow from said ventilator unit from said second test gas flow pattern, said second response gas flow pattern and said transfer function; and further compensating said compensated settings dependent on said influence of the respiratory system.

4. A method as claimed in claim 3 wherein said first test gas flow pattern is the same as said second test gas flow pattern.

5. A method as claimed in claim 3 wherein said ventilator unit is operable in a plurality of ventilation modes and wherein said second test gas flow pattern has a spectrum corresponding to different frequency spectra respectively present in said plurality of ventilation modes.

6. A method as claimed in claim 1 wherein said ventilator unit is operable in a plurality of ventilation modes and wherein said first test gas flow pattern has a spectrum corresponding to different frequency spectra respectively present in said plurality of ventilation modes.

7. A method as claimed in claim 1 wherein the step of determining said transfer function comprises determining said transfer function from a plurality of pre-programmed model structures for said connection system and selecting a model structure from said plurality of model structures having a highest correlation as said transfer function.

8. A method as claimed in claim 1 wherein the step of determining said transfer function comprises determining said transfer function from a plurality of linear and nonlinear pre-programmed model structures for said connection system and selecting a model structure from said plurality of model structures having a highest correlation as said transfer function.

9. An apparatus for regulating the supply of breathing gas to and the removal of expired gas from the respiratory system of a subject in a ventilator system having a ventilator unit and a connection system connectable to a subject's respiratory system said connection system having a transfer function associated therewith identifying an influence of said connection system on gas pressure and gas flow in said connection system, said apparatus comprising:

- means for setting a test gas flow pattern in said ventilator unit and for supplying gas with said test flow pattern to said connection system;
- means for measuring a response gas flow pattern arising from said test gas flow pattern;
- means for determining said transfer function from said test gas flow pattern and said response gas flow pattern;
- means for selecting a therapeutic gas flow pattern; and
- means for setting a compensated gas flow pattern at said ventilator unit, dependent on said transfer function, for producing said selected therapeutic gas flow pattern, via said connection system, at a subject's respiratory system.

10. An apparatus as claimed in claim 9 further comprising a lung model having known characteristics connectable to said connection system during supply of said test gas flow pattern.

11. An apparatus as claimed in claim 10 wherein said means for supplying gas with said test gas flow pattern to said connection system comprises means for supplying gas with said test gas flow pattern to said connection system with said lung model connected to said connection system as a first test gas flow pattern, and said apparatus further comprising:

- means for supplying a second test gas flow pattern from said ventilator unit to a subject's respiratory system via said connection system with said lung model removed from said connection system;
- wherein said means for measuring comprises means for measuring a second response gas flow pattern arising from said second test gas flow pattern;
- means for determining an influence of a subject's respiratory system on gas flow from said ventilator unit from said second test gas flow pattern, said second response gas flow pattern and said transfer function; and
- means for further compensating said compensated settings dependent on said influence of a subject's respiratory system.

12. An apparatus as claimed in claim 11 wherein said means for supplying gas to said connection system comprises means for supplying gas with said first test gas flow pattern the same as said second test gas flow pattern.

13. An apparatus as claimed in claim 9 wherein said means for determining said transfer function comprises means for determining said transfer function from a plurality of pre-programmed model structures for said connection system and for selecting a model structure from said plurality of model structures having a highest correlation as said transfer function.

14. An apparatus as claimed in claim 9 wherein said means for determining said transfer function comprises means for determining said transfer function from a plurality of linear and non-linear pre-programmed model structures for said connection system and for selecting a model structure from said plurality of model structures having a highest correlation as said transfer function.

15. A method for determining at least one mechanical lung parameter of a respiratory system of a subject in a ventilator system having a ventilator unit connectable to the respiratory system of the subject, said method comprising the steps of:

- connecting a connection system to said ventilator unit, said connection system having a transfer function associated therewith identifying an influence of said connection system on gas pressure and gas flow in said connection system;
- setting a test gas flow pattern in said ventilator unit and supplying gas with said test gas flow pattern to said connection system;
- measuring a response gas flow pattern arising from said test gas flow pattern;
- determining said transfer function from said test gas flow pattern and said response gas flow pattern;
- connecting said connection system to the respiratory system of the subject;
- supplying a second test gas flow pattern from said ventilator unit to the subject's respiratory system via said connection system;
- measuring a second response gas flow pattern arising from said second test gas flow pattern;
- determining said mechanical lung parameter from said second gas flow pattern, said second response gas flow pattern and said transfer function.

16. A method as claimed in claim 15 wherein said first gas flow pattern is the same as the second test gas flow pattern.

17. A method as claimed in claim 15 wherein the mechanical lung parameter is resistance.

18. A method as claimed in claim 15 wherein the mechanical lung parameter is compliance.

19. A method as claimed in claim 15 wherein the step of determining said transfer function comprises determining said transfer function from a plurality of pre-programmed model structures for said connection system and selecting a model structure from said plurality of model structures having a highest correlation as said transfer function.

20. A method as claimed in claim 15 wherein the step of determining said transfer function comprises determining said transfer function from a plurality of linear and non-linear pre-programmed model structures for said connection system and selecting a model structure from said plurality of model structures having a highest correlation as said transfer function.

* * * * *